(12) United States Patent
Hubner et al.

(10) Patent No.: US 7,048,439 B2
(45) Date of Patent: May 23, 2006

(54) ADJUSTABLE LINKAGE MOUNTING ASSEMBLY FOR DENTAL X-RAY ASSEMBLY

(75) Inventors: Henry Hubner, Amityville, NY (US); Walter Gross, Massapequa, NY (US)

(73) Assignee: Air Techniques, Inc., Hicksville, NY (US)

( * ) Notice: Subject to any disclaimer, the term of this patent is extended or adjusted under 35 U.S.C. 154(b) by 47 days.

(21) Appl. No.: 10/818,913

(22) Filed: Apr. 6, 2004

(65) Prior Publication Data

US 2004/0228449 A1 Nov. 18, 2004

Related U.S. Application Data

(60) Provisional application No. 60/460,620, filed on Apr. 7, 2003.

(51) Int. Cl.
*A61B 6/14* (2006.01)
*H05G 1/02* (2006.01)
*A47F 5/00* (2006.01)

(52) U.S. Cl. ............... 378/191; 378/197; 378/196; 248/288.51

(58) Field of Classification Search ........... 378/191, 378/196–198; 188/68, 67, 61; 248/288.51
See application file for complete search history.

(56) References Cited

U.S. PATENT DOCUMENTS

| 1,580,320 | A | * | 4/1926 | Osborn | 378/196 |
|---|---|---|---|---|---|
| 3,025,401 | A | * | 3/1962 | Lauterbach | 378/98 |
| 3,902,575 | A | * | 9/1975 | Nelson et al. | 188/67 |
| 4,452,342 | A | * | 6/1984 | Schindel | 188/69 |
| 5,681,018 | A | * | 10/1997 | Hoftman | 248/125.8 |

* cited by examiner

*Primary Examiner*—Edward J. Glick
*Assistant Examiner*—Krystyna Suchecki
(74) *Attorney, Agent, or Firm*—Clifford G. Frayne; Louis E. Marn

(57) ABSTRACT

These and other objects of the present invention achieved by adjustable linkage mounting member for shaft members associated with articulating positioning arm members of a dental x-ray assembly wherein each adjustable linkage mounting member is comprised of a housing member mounted within a chamber thereof for receiving a shaft member of a positioning arm member and having a brake shoe disposed in the chamber in frictional contact with the shaft member and wherein frictional contact is adjustable in response to a threaded member disposed in the chamber.

6 Claims, 3 Drawing Sheets

ADJUSTABLE LINKAGE MOUNTING ASSEMBLY FOR DENTAL X-RAY ASSEMBLY

RELATED APPLICATIONS

Applicant claims the benefit of provisional application Ser. No. 60/460,620, filed Apr. 7, 2003.

BACKGROUND OF THE INVENTION

1. Field of the Invention

This invention relates to a dental x-ray assembly, and more particularly, to an adjustable linkage mounting assembly for articulating arms of a dental x-ray assembly.

2. Description of the Prior Art

In dental operatories, a dental x-ray system is generally cantileverly positioned by a vertically-disposed shaft member in a mounting frame or bracket mounted to a vertical support member, such as a wall. The dental x-ray assembly includes a horizontally-disposed extension arm member mounted to the vertically-disposed shaft member disposed for rotation in the mounting assembly. At an end of the horizontal-disposed extension arm member remote from the mounting member, there is included vertically-disposed inner and outer positioning arm members articularly mounted therebetween to each other. To the outer arm member, th ere is provided an x-ray tube head assembly extending downwardly from an end of the outer arm member for appropriately positioning an x-ray generating member of the x-ray tube head assembly at a point proximate a patient's oral cavity to effect imaging of such preselect portion thereof.

The articulating arms have been provided with springs to counter balance the weight of the tube head. However, the spring force and mechanical advantage of the spring force relative to the weight of the tube head vary continuously throughout the motion of the articulating arms. It is therefore difficult to compensate for the weight of the tube head for all of the positions of bar linkages necessary in order to obtain all of the necessary x-rays of the patient's oral cavity. The x-ray tube head has a tendency to rise or fall in certain positions which is detrimental to the operation for obtaining accurate x-ray information.

One solution to the problem was an attempt to dampen the system through the use of a friction washer positioned between the articulating arms on the far linkages thereto with a threaded fastener. However such solution suffered from the disadvantage that it is sensitive to adjustments and friction forces change rapidly with wear.

OBJECTS OF THE INVENTION

It is an object of the present invention is to provide an improved adjustable linkage mounting assembly for articulating positioning arm members of a dental x-ray assembly obviating the problems of the prior art.

Another object of the present invention is to provide an improved adjustable linkage mounting assembly for articulating positioning arm members of a dental x-ray assembly permitting facile adjustment to provide accurate positioning of an associated x-ray tube head assembly.

Yet another object of the present invention is to provide an improved adjustable linkage mounting assembly for articulating positioning arm members of a dental x-ray assembly substantially eliminating miscellaneous movement of the x-ray tube head assembly once desired positioning thereof is achieved.

A still further object of the present invention is to provide an improved adjustable linkage mounting assembly for articulating positioning arm members of a dental x-ray assembly facilely adjustable over the life of the dental x-ray assembly.

SUMMARY OF THE INVENTION

These and other objects of the present invention achieved by adjustable linkage mounting member for shaft members associated with articulating positioning arm members of a dental x-ray assembly wherein each adjustable linkage mounting member is comprised of a housing member mounted within a chamber thereof for receiving a shaft member of a positioning arm member and having a brake shoe disposed in the chamber in frictional contact with the shaft member and wherein frictional contact is adjustable in response to a threaded member disposed in the chamber.

BRIEF DESCRIPTION OF THE DRAWINGS

Other objects and advantages of the present invention will become more readily apparent from the following description thereof when taken with the accompanying drawings, wherein.

DETAILED DESCRIPTION OF THE INVENTION

Figure 1:
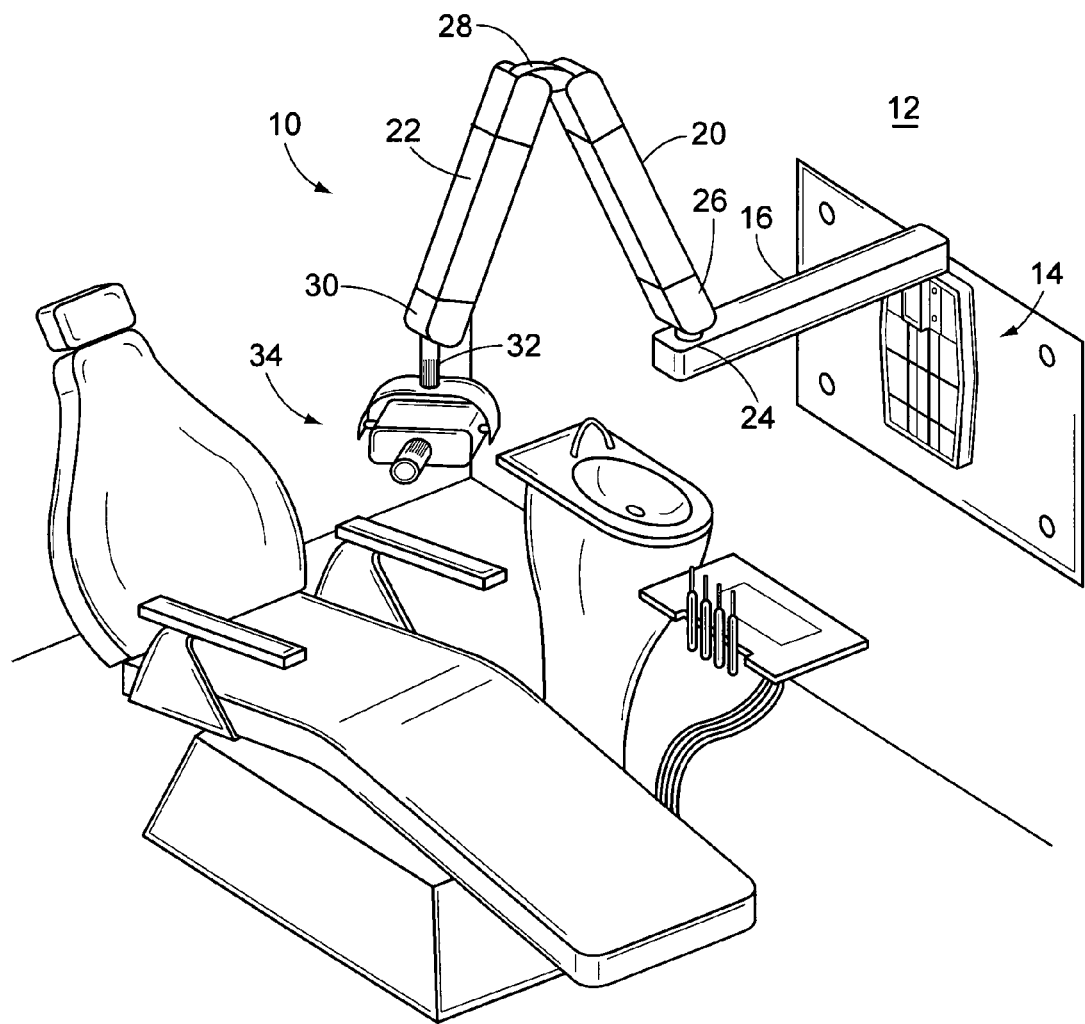
FIG. 1 is a typical prospective view of a typical dental operatory including a dental x-ray assembly having articulating positioning arm members for a dental x-ray tube head assembly.

Referring now to FIG. 1, there is illustrated a dental x-ray assembly, generally indicated as 10, mounted to a vertical support member 12, such as a wall, by a mounting assembly, generally indicated as 14, positioned within a dental operatory. The mounting assembly 14 is the subject matter of copending U.S. Application (P/4627), hereby incorporated by reference. The dental x-ray assembly 10 includes a horizontally-disposed extension arm member 16 mounted for horizontal rotation within the mounting member 14.

The extension arm member 16 supports articularly-mounted inner and outer positioning members 20 and 22 as more fully hereinafter described. An end of the extension arm member 16 remote from the mounting assembly 14 is provided with an upwardly-extending support arm member 24 including an adjustable linkage mounting member 26 connected to a lower portion of the inner positioning arm member 20 permitting vertical movement thereof. Upper end portions of the inner and outer positioning members 20 and 22 are connected to an intermediated adjustable linkage mounting member 28 permitting vertical movement therebetween. A lower end portion of the outer positioning member 22 is connected to an adjustable linkage mounting member 30 of a vertically-disposed arm member 32 supporting the x-ray tube assembly, generally indicated as 34.

Figure 2:
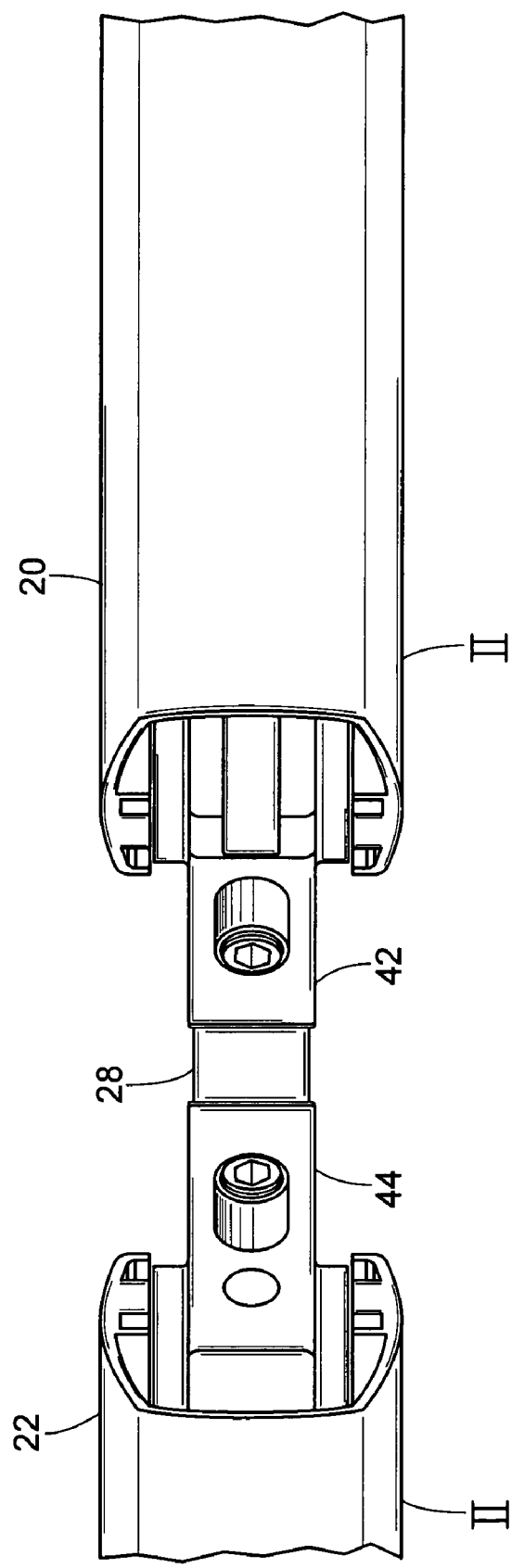
FIG. 2 is a partial top elevational view of an intermediate adjustable linkage mounting member for inner and outer articulating positioning arm members.
Figure 3:
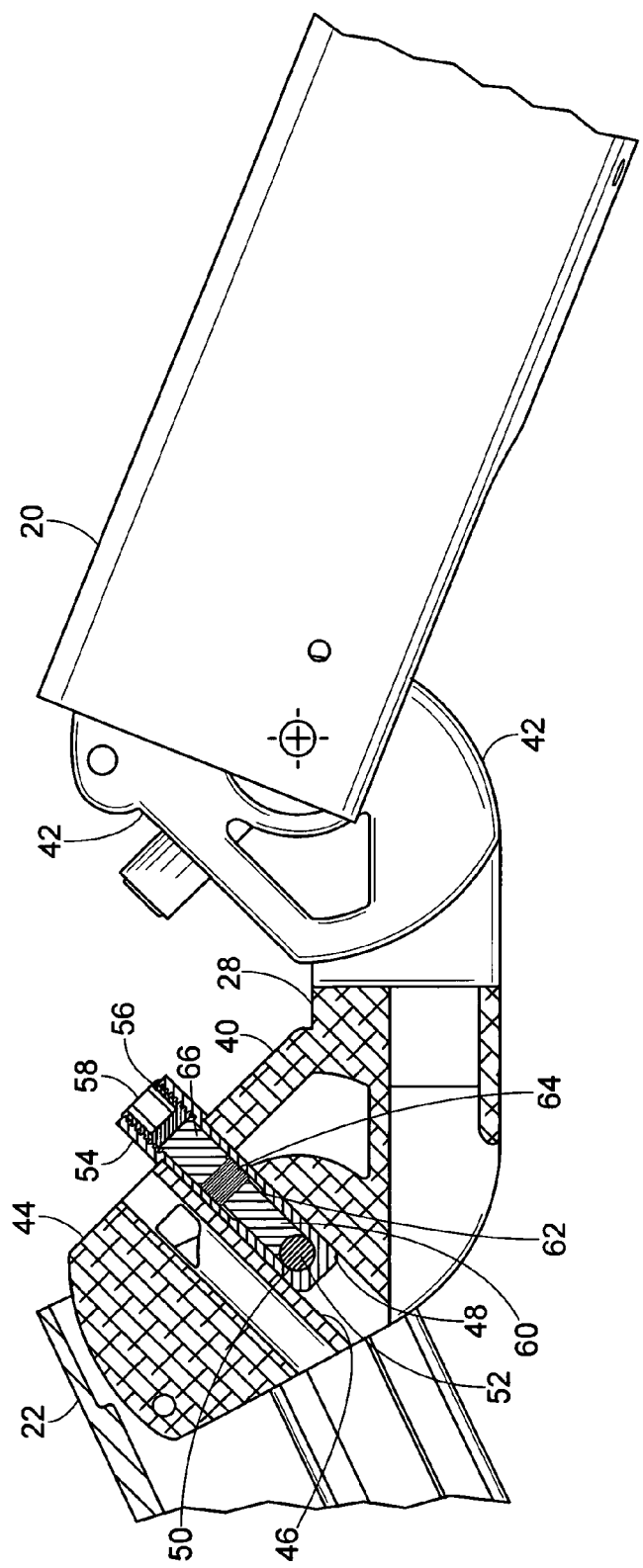
FIG. 3 is a partial cross-sectional side view of the intermediate adjustable linkage mounting member taken along the lines II—II of FIG. 2.

Referring now to FIGS. 2 and 3, the intermediate adjustable linkage mounting member 28 is comprised of main body portion 40 having an upwardly-extending arm portion 42 cooperating with an upper end portion of the inner positioning member 20 and an upwardly-extending arm portion 44 cooperating with an upper end portion of the outer positioning member 22. An arm portion, referring particular to the arm portion 44 of the intermediate linkage mounting member 40 in FIG. 3, is formed along a major axis thereof with a cylindrically-shaped channel 46 extending downwardly at an angle of about 45 degrees for fixedly positioning a cylindrically-shaped housing member 48 therein. A lower portion of the cylindrically-shaped housing member is formed with a U-shaped channel 50 for positioning a shaft member 52 mounted in an upper end portion of the outer positioning member 22.

The cylindrically-shaped housing member is formed with a cap portin 54 extending outwardly from the arm portion 44 of the intermediate adjustable linkage member 40. An internal surface 56 of the cap portion 54 is threaded to receive a cooperating threaded screw member 58. Disposed within the cylindrically-shaped channel 46, there is provided a cylindrically-shaped braking shoe member 60 having a semi-circularly contact surface 62 in frictional contact with the shaft member 52. A spring washer set 64 providing biasing forces is positioned in the channel 46 on the brake shoe member 60 with a compression member 66 disposed between the spring washer set 64 and the threaded adjusting screw member 58.

In operation, clockwise rotation of the threaded screw member 56 causes same to be incrementally inserted into the cylindrically-shaped channel 46 thereby applying pressure on the compression member 66 with concomitant pressure applied via biasing spring washer set 64 and thus the brake shoe member 60 to increase frictional engagement thereof with the shaft member 52 thereby to increase required rotational forces for rotational movement of the outer positioning arm member 22. The biasing spring washer set 64 provides a measure of pressure maintenance during use, however, it will be understood that adjustment to pressure maintenance may be made during use of the dental x-ray assembly 10 including replacement of the brake shoe member 60 or other items within the cylindrically-shaped channel 46 during life of usage of the dental x-ray assembly.

While the present invention has been described with reference to the frictional contacting assemblage of arm portion 44 of the intermediate adjustable linkage mounting member 40, the outer positioning member 22, it is understood that like frictional contacting assemblages are provided with respect to the other adjustable linkage mounting members 24, 30 and arm portion 42 connected to the inner and outer arm positioning members 20 and 22.

While the present invention herein has been described in connection with an exemplary embodiment thereof, it will be understood that many modifications thereof will be apparent to those of ordinary skill in the art and that this application is intended to cover any adaptations or variations thereof. Therefore, it is manifestly intended that this invention be only limited by the claims and the equivalents thereof.

What is claimed is:

1. A dental x-ray assembly for a dental operatory, said dental x-ray assembly having articulating positioning arm members for an x-ray tube assembly said articulating positioning arm members connected within said dental x-ray assembly by adjustable linkage mounting members for receiving shaft members associated with said articulating positioning arm members, for articulating and positioning said articulating positioning arm members relative to each other, each of said adjustable linkage mounting members comprised of a housing member mounted within a chamber of said adjustable linkage mounting members for receiving a shaft member of said articulating positioning arm member, and a means for adjustable frictional engagement with said shaft member in response to a means rotatably disposed on said housing member, said chamber is cylindrically-shaped and said housing member is cylindrically-shaped with a U-shaped end portion for receiving said shaft of said articulating positioning arm member, said means for frictionally engaging said shaft member is a cylindrically-shaped brake shoe member having a semi-circular end surface for cooperating with a circumference of said shaft member.

2. The dental x-ray assembly as defined in claim 1 wherein said means rotatably disposed on said housing member includes an end cap portion extending outwardly from said linkage mounting member formed with an internal threaded surface for receiving a threaded member included in said adjusting means.

3. The dental x-ray assembly as defined in claim 2 and further including a cylindrically-shaped compression member disposed in said chamber in abutting relationship to said threaded member for movement in response to rotational movement of said threaded member within said housing member.

4. The dental x-ray assembly as defined in claim 3 wherein a spring washer set is positioned within said chamber between said brake shoe member and said compression member to facilitate adjustment of frictional contact of said brake shoe member with said shaft.

5. The dental x-ray assembly as defined in claim 1 wherein said adjustable linkage mounting member includes an outwardly extending arm portion wherein said chamber is disposed in said arm portion downwardly at an angle with respect to a major axis of said adjustable linkage mounting member.

6. The dental x-ray assembly as defined in claim 5 wherein said angle is 45 degrees with respect to said major axis of said adjustable linkage mounting member.

* * * * *